United States Patent [19]

Edwards

[11] Patent Number: 4,465,877

[45] Date of Patent: Aug. 14, 1984

[54] MAGNESIUM CATALYZED ALKOXYLATION OF ALKANOLS IN THE PRESENCE OF ALKOXYLATE REACTION ACTIVATORS

[75] Inventor: Charles L. Edwards, Houston, Tex.

[73] Assignee: Shell Oil Company, Houston, Tex.

[21] Appl. No.: 519,884

[22] Filed: Aug. 3, 1983

[51] Int. Cl.$^3$ .............................................. C07C 41/03
[52] U.S. Cl. .................................... 568/618; 568/622; 568/678; 568/679
[58] Field of Search ................ 568/618, 622, 678, 679

[56] References Cited

U.S. PATENT DOCUMENTS 3,752,857 8/1973 Milligan .
3,972,948 8/1976 Laemmle et al. .
4,134,854 1/1979 Milligan .

Primary Examiner—Howard T. Mars

[57] ABSTRACT

Alkanol alkoxylates having utility, for instance, as nonionic surfactants in detergent formulations are prepared by the reaction of $C_6$ to $C_{30}$ alkanols with $C_2$ to $C_4$ alkylene oxides in the presence of a catalytically effective amount of one or more soluble basic compounds of magnesium and additionally in the presence of as a reaction activator at least about 2 percent by mole, calculated on moles of alkanol, of alkoxylates of one or more $C_1$ to $C_{30}$ alkanols having in the alkoxylate molecules from one to about 30 adducts of one or more alkylene oxides selected from the class consisting of $C_2$ to $C_4$ alkylene oxides.

20 Claims, No Drawings

MAGNESIUM CATALYZED ALKOXYLATION OF ALKANOLS IN THE PRESENCE OF ALKOXYLATE REACTION ACTIVATORS

This is a continuation of application Ser. No. 334,092 filed Dec. 23, 1981, now abandoned.

BACKGROUND OF THE INVENTION

This invention relates to the preparation of alkanol alkoxylates by the addition reaction of alkylene oxides with alkanols in the presence of basic catalysts. More specifically, this invention is directed to a process for conducting the alkoxylation reaction of alkanols with alkylene oxides in the presence of basic magnesium-containing catalysts.

Alkanol alkoxylates (or simply alkoxylates, as the terminology is alternatively applied herein) are known materials having utility, for instance, as solvents, surfactants, and chemical intermediates. Alkoxylates in which the alkyl group has a number of carbon atoms in the detergent-range, i.e., from about 8 to 20, are common components of commercial cleaning formulations for use in industry and in the home.

Under conventional practice, alkoxylates are typically prepared by the addition reaction of alkylene oxides with alkanols. In the particular case of the preparation of an ethoxylate (represented by formula III below) the addition of a number (n) of ethylene oxide molecules (formula II) to a single alkanol molecule (formula I) is illustrated by the equation

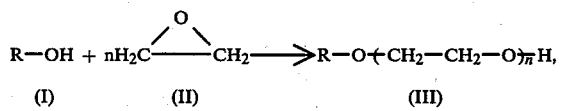

wherein R is alkyl and n is an integer equal to or greater than one. The product of such an alkoxylation reaction is a mixture of various alkoxylate molecules having a variety of alkylene oxide adducts, i.e., a mixture of compounds with different values of n.

Alkoxylation reactions between alkylene oxides and alkanols are known to be necessarily carried out in the presence of a catalyst, which may be either of acidic or basic character. Suitable basic catalysts are known to include the soluble basic salts of the alkali metals of Group I of the Periodic Table, e.g., lithium, sodium, potassium, rubidium, and cesium, and the soluble basic salts of certain of the alkaline earth metals of Group II, e.g., barium, strontium, and calcium. With particular regard to magnesium-containing catalysts as are employed in the process of this invention, the most relevant teachings of the art, specifically, those of U.S. Pat. No. 4,239,917, U.S. Pat. No. 4,210,764, and U.S. Pat. No. 4,233,164 on alkoxylation reactions catalyzed by barium and strontium compounds, indicate only that certain basic magnesium compounds do not effectively promote the alkoxylation of detergent-range alkanols. Other references which describe alkoxylation reactions catalyzed by alkaline earth metal compounds, for instance, the published European patent applications Nos. 26,544, 26,546, and 26,547 and U.S. Pat. Nos. 3,830,850 and 3,637,869 do not mention the use of magnesium compounds as alkoxylation catalysts.

Numerous acidic substances, including broadly the Lewis acid or Friedel-Crafts catalysts and specifically the compound magnesium perchlorate, are also known as effective alkoxylation catalysts. However, the use of acid catalysts is undesirable in several processing aspects. For instance, the acidity of the reaction mixture catalyzes side reactions to produce relatively large amounts of polyalkylene glycols. The acid catalysts also react directly with components of the alkoxylation mixture to yield organic derivatives of the acids which for reasons such as toxicity are not acceptable in the alkoxylate product. Furthermore, efficient use of acid catalysts is generally limited to the alkoxylation of secondary alkanols and to the preparation of alkoxylates having an average number of ethylene oxide adducts that is less than about 2 or 3.

SUMMARY OF THE INVENTION

It has now been found that alkanol alkoxylates are prepared by the addition reaction between an alkylene oxide reactant and an alkanol reactant carried out in the presence of soluble basic magnesium catalysts and further in the presence of a specified reaction activator. In the absence of the activator, basic magnesium compounds are not suitably effective as catalysts for the alkoxylation. Very advantageously, the activator is an addition reaction product of the alkanol and the alkylene oxide reactants, or, in other words, an alkoxylate of the sort prepared by the process of the invention.

Accordingly, the present invention is a process for the preparation of alkanol alkoxylates which comprises reacting an alkanol reactant comprising one or more alkanols having carbon numbers in the range from 6 to 30, inclusive, with an alkylene oxide reactant comprising one or more alkylene oxides having carbon numbers in the range from 2 to 4, inclusive, in the presence of a catalytically-effective amount of one or more soluble basic compounds of magnesium and additionally in the presence of, as a reaction activator, at least about 2.0 percent by mole, calculated on alkanol reactant, of one or more alkoxylates as are produced by an alkoxylation reaction between $C_1$ to $C_{30}$ alkanols and $C_2$ to $C_4$ alkylene oxides.

DESCRIPTION OF THE PREFERRED EMBODIMENTS

The process of this invention is directed to discoveries associated with the activation of an alkoxylation reaction between $C_6$ to $C_{30}$ alkanols and $C_2$ to $C_4$ alkylene oxides catalyzed by soluble, basic compounds of magnesium. Apart from aspects relating to the use of certain specified catalysts and reaction activators, the process of the invention is as a general rule suitably conducted under such processing procedures and reaction conditions are known to the art for base-catalyzed alkoxylation reactions.

Still, for purposes of the invention, particular preferences may be stated for certain processing parameters. For instance, the alkoxylation reaction is preferably carried out at a temperature in the range from about 90° to 250° C. A more preferred range is that from about 130° to 210° C., while a temperature between about 150° and 190° C. is still more preferred. Considered most preferred is a reaction temperature in the range from about 165° to 175° C. Although the pressure under which the alkoxylation reaction is conducted is not critical to the invention, a total pressure in the range from about 0 to 150 psig is preferred. Under preferred conditions of temperature and pressure, the alkanol reactant and the alkoxylate reaction activator are generally liquid and the alkylene oxide reactant a vapor. The alkoxylation is then most conveniently conducted by contacting gaseous alkylene oxide with a liquid solution of the magnesium compound and the alkoxylate activaor in the alkanol. Since, as is known, there is danger of explosion in alkylene oxides maintained in concentrated form at elevated temperature and pressure, the partial pressure of the alkylene oxide in the vapor phase is preferably limited, for instance, to less than about 60 psia, and this reactant is diluted with an inert gas such as nitrogen, for instance, to a vapor phase concentration of about 50 percent or less. The reaction can, however, be safely accomplished at greater alkylene oxide concentration, greater total pressure and greater partial pressure of alkylene oxide if suitable precautions, known to the art, are taken to manage the risks of explosion. A total pressure of between about 40 and 110 psig, with an alkylene oxide partial pressure between about 15 and 60 psia, is particularly preferred, while a total pressure of between about 50 and 90 psig, with an alkylene oxide partial pressure between about 20 and 50 psia is considered more preferred.

The alkanol reactant that is suitable for use in practice of the present invention comprises, in the broad sense, one or more of the same $C_6$ to $C_{30}$ alkanols as have been heretofore recognized as suitable for alkoxylation by reaction with alkylene oxides in the presence of basic catalysts, for example, those alkanols described as suitable for this purpose in the above-referenced U.S. patents and published European patent applications. Primary alkanols are particularly preferred, largely on the basis of rate of the alkoxylation reaction. For reasons relating to the utility of the product alkoxylates in detergent formulations, preference may be expressed for alkanols within further restricted carbon number ranges. Thus, alkanols in the $C_7$ to $C_{22}$ range are preferred reactants, while those in the $C_8$ to $C_{18}$ range are considered more preferred and those in the $C_{10}$ to $C_{16}$ range most preferred. Still further preference for reason of product utility may be stated for alkanol reactants in which greater than about 50 percent, more preferably greater than about 70 percent, and most preferably greater than about 90 percent of the alkanol molecules are of linear (straight-chain) carbon structure. Mixtures containing a variety of such alkanols, differing, for instance, with respect to carbon number and branching in the carbon chain, are suitable for purposes of the process of the invention and are in most cases preferred because of commercial availability.

The alkylene oxide (epoxide) reactant utilized in the process of the invention comprises one or more alkylene oxides, preferably the vicinal alkylene oxides having from 2 to 4 carbon atoms, including ethylene oxide, propylene oxide, and the 1,2- and 2,3-butylene oxides. Particularly preferred are ethylene oxide and propylene oxide, while the use of ethylene oxide is most preferred. Mixtures of alkylene oxides are suitable, in which case the product of the invention will be a mixed alkoxide.

The alkoxylation reaction of the process of the invention is necessarily carried out in the presence of, as catalyst, a soluble, basic compound of magnesium. For purposes of practicing the invention, addition may be made to the alkoxylation reaction mixture of either a magnesium compound which is soluble and basic per se or a precursor which is converted to a soluble basic form of magnesium upon interaction with the alkoxylation process reactants and/or the specified reaction activator. The catalyst is described as soluble in the sense that it is soluble in a mixture of liquid alkanol reactant and alkoxylate (including both the alkoxylate utilized as activator and that produced in the process) to the extent necessary to promote the desired reaction. At least about 0.1 percent by mole (%m) of the magnesium compound, calculated on moles of total alkanol reactant, is typically necessary for the desired catalytic effect. Preferably, the magnesium compound is present in the reaction mixture in a quantity between about 0.2 and 20%m calculated on alkanol, while a quantity between about 0.5 and 15%m is more preferred and between about 1.5 and 10%m is considered most preferred. As a rule, the rate of the alkoxylation reaction increases as the invention is carried out with increasing quantities of the catalyst. The catalyst is described as basic in the conventional sense, indicating that a hydrolyzed sample of an alkoxylation reaction mixture containing the magnesium compound in a catalytically-effective quantity (e.g., a 10%w solution of the reaction mixture in water) has a pH greater than 7.0. For purposes of the invention, the overall reaction mixture is of basic pH. Examples of specific soluble, basic catalysts suitable for introduction into the reaction mixture include the reaction products of magnesium with various alcohols (for instance, alcoholates such as magnesium alkoxides and phenoxides), as well as ammoniate, amide, thiolate, thiophenoxide and nitride compounds. Preferred for use as catalyst (or catalyst precursor) are the alcoholates, while the alkoxides in particular are considered more preferred. Each alkoxy group of such alkoxides has a carbon number that is preferably in the range from 1 to about 30, more preferably in the range from 1 to about 6. The most preferred alkoxides are those having $C_1$, $C_2$ or $C_3$ alkyl groups, i.e., magnesium methoxide, ethoxide and propoxide. Representative of suitable catalyst precursors which are not per se soluble and/or basic but which are converted into soluble, basic compounds in the alkoxylation reaction mixture are the thiocyanates and the carboxylates, such as the formate, acetate, oxalate, citrate, benzoate, laurate, and stearate. Without intention that the invention be limited to one theory or mechanism of operation, it is speculated that soluble, basic magnesium compounds which are added to or formed in the reaction mixture function to aid in the formation (by transalcoholysis reaction, or otherwise) of alkoxides of the alkanol reactant and/or of the alkoxylate activator, which then more directly promote the desired alkoxylation.

The alkoxylation process of the invention is necessarily carried out in the presence of the specified reaction activator. In the absence of the activator, the magnesium catalyst fails to effectively promote the desired alkoxylation reaction between alkanol and alkylene oxide reactants. Like the alkoxylate product of the process of the invention, the activator comprises one or more compounds of the general formula $R'-O-C_xH_{2x}-O)_nH$. For purposes of defining suitable activators, $R'$ is as an alkyl group of one to 30 carbon atoms, inclusive, n represents an integer in the range from 1 to about 30, and x (in each individual $-C_xH_{2x}-O-$ moiety) is an integer in the range from 2 to 4, inclusive. In alternative terms, the activator is described as the alkoxylation reaction product of one or more $C_1$ to $C_{30}$ alkanols with from one to about 30 moles of one or more $C_2$ to $C_4$ alkylene oxides.

In the course of the alkoxylation reaction of the process of the invention, the alkoxylate activator as well as the alkanol reactant reacts with the alkylene oxide reactant. For reasons relating to properties of the process product mixture, the (higher) alkoxylate formed by reaction of the (lower) alkoxylate activator with alkylene oxide is subject to the same preferences, in terms of carbon number of the alkyl group ($R'$) and adduct number (n), as is the alkoxylate formed during practice of the invention by reaction of the alkanol reactant with the alkylene oxide reactant. (Consideration is given to the contribution of such higher alkoxylates of the activator to properties of the process product mixture because it is in most cases impractical to separate this higher alkoxylate from the principal product formed through alkoxylation of the alkanol reactant.) Thus, the carbon number of the alkyl group $R'$ is preferably in the range from about 6 to 30, more preferably in the range from about 8 to 18, and most preferably in the range from about 10 to 16. Expressed in another manner, the activator comprises one or more alkoxylation products of alkanols which are preferably in the $C_7$ to $C_{22}$ range, more preferably in the $C_8$ to $C_{18}$ range and most preferably in the $C_{10}$ to $C_{16}$ range. Activators which are the alkoxylate products of alkanols of at least about six carbon atoms are also preferred for a favorable influence on alkoxylation reaction rate. It is particularly desirable that in the practice of an embodiment of the invention, the carbon number (or carbon number distribution) of the alkyl $R'$ group of the alkoxylate activator be essentially the same as that of the alkanol reactant utilized. In order to obtain a product mixture in which the higher alkoxylate formed from the activator has an adduct number distribution similar to that of the alkoxylate formed from the alkanol reactant, activators of relatively low adduct number, for instance, an activator characterized by an average adduct number less than 5, are preferred. More preferred are activators having an average adduct number less than about 3, while activators having an average adduct number less than about 2 are considered most preferred. Again, as indicated above, these preferences relate to desired properties of the product and not to the operability in the use of the materials as reaction activators for purposes of invention.

The source of the activator and the manner in which it is introduced into the reactant and catalyst mixture are not critical to the invention. In like manner to the catalyst, the activator is suitably either added directly to the reaction mixture or formed in situ by interaction of another added substance with the process reactants and/or catalyst. In a particularly preferred mode of operation, an alkoxylate activator may be formed in situ in the reactants to be utilized by first carrying out a limited alkoxylation reaction between these reactants in the presence of a catalyst (other than magnesium) capable of promoting alkoxylation in the absence of an activator. For instance, a basic alkali metal compound (e.g. sodium or potassium hydroxide), or a basic compound of another alkaline earth metal (e.g., of barium or strontium), or a Lewis acid catalyst (e.g., a halide of boron, antimony, tungsten, iron, nickel, zinc, tin, aluminum, titanium or molybdenum) can be utilized to promote alkoxylation to yield an alkoxylate, suitable as a reaction activator, in the desired quantity. An advantage of such an operation is the formation of an activator having the same carbon number or carbon number distribution in the alkyl group ($R'$ in the above formula) as that of the alkanol reactant, and also having an average adduct number that is very low, e.g., most preferably in the range from 1 to about 2. After formation of the activator, the acid or base catalyst can be neutralized, and, if desired, removed, before the alkoxylation process of the invention is carried out in the presence of the magnesium catalyst. In certain cases, the activator is also suitably formed in situ by the introduction, into a mixture of the alkanol reactant, alkylene oxide reactant, and magnesium catalyst, of a reaction initiator other than an alkoxylate activator, for instance, an ether (other than an alkoxylate) or another compound which, in the presence of the magnesium catalyst will stimulate the reaction between alkanol and alkylene oxide reactants to produce a small amount (e.g., 2 to 7%m) of the desired alkanol alkoxylate product. This small degree of alkoxylation of the alkanol reactant inherently produces an alkoxylate activator in the quantity specified herein and the reaction thereafter proceeds in accordance with the invention. In terms of combination of factors, including contamination of the reaction mixture, effectiveness of reaction activation, and overall process efficiency and convenience, however, introduction into the reaction mixture of such alkoxylates of lesser carbon number, other ethers and the like to produce the specified alkoxylate activator in situ is not a preferred method of operation.

For purposes of this invention the reaction activator is present in the reaction mixture in a quantity of at least about 2 percent by mole (%m) calculated on moles of alkanol reactant. Larger amounts of activator reduce or eliminate the induction time which may be encountered before alkoxylation commences. Quantities of activator of at least about 3%m are preferred, while quantities of at least about 5%m are more preferred quantities of at least about 6%m are still more preferred, and quantities of at least about 7%m are considered most preferred. The minimum amount of activator necessarily present in the reaction mixture for purposes of the invention is believed to be dependent both upon the relative quantity of activator to alkanol and upon the relative quantity of activator to magnesium catalyst. Smaller quantities of activator may be effective with relatively low catalyst concentrations, although with both an increased induction period and a low alkoxylation reaction rate. There is no upper limit upon the quantity of activator which can be employed. The invention is suitably applied to the alkoxylation of both the alkanol reactant component and the alkoxylate activator component in mixtures comprising substantially greater quantities of activator than alkanol, for instance, mixtures prepared by alkoxylation of alkanols in the presence of catalysts other than magnesium compounds.

In terms of processing procedures, the invention is preferably carried out by mixing together the magnesium catalyst or catalyst precursor, the liquid alkanol reactant and the liquid alkoxylate activator and then contacting the resulting solution with gaseous ethylene oxide at the specified temperature and pressure. In one preferred mode of operation, the catalyst and the activator are first mixed before they are contacted with either of the reactants. If, on the other hand, the catalyst and activator are individually introduced into the reaction mixture it is preferred that the alkoxylate activator be put into solution in the liquid reactant phase in the specified quantity before the magnesium catalyst (or its precursor) is mixed with this liquid phase. Upon addition of the preferred quantities of magnesiun catalyst to the alkanol reactant in the absence of the activator, the resulting mixture commonly forms a viscous gel. While the subsequent addition to the gel mixture of the alkoxylate activator in the specified quantity acts to break this gel, the gel formation leads to handling problems which can be avoided simply by reversing the order of the addition of the catalyst and activator to the alkanol.

Following the preparation of a solution of the catalyst and activator in the alkanol in the relative quantities herein specified, the solution is contacted at the desired temperature and pressure with the alkylene oxide reactant. An induction time may be encountered before the alkoxylation reaction commences. Increased quantities of activator function to shorten the induction period. As the alkylene oxide is taken up in the reaction, additional alkylene oxide is added, conveniently at a rate which maintains an approximately constant reaction pressure. Addition of alkylene oxide and its reaction with alkanol to form alkoxylate is continued until the product reaches the average alkylene oxide adduct number desired for the particular process. Generally, although not necessarily, the invention is best utilized in the preparation of alkoxylates having an average adduct number in the range of between about 1 and 30, expressed in terms of the total mols of alkylene oxide reacted per mol of alkanol. For reasons relating to utility of the alkoxylate in the broadest commercial applications the process is continued to yield a product having an adduct number that is preferably between about 2 and 20, more preferably between about 3 and 15, most preferably between about 4 and 12. The time required to complete a process in accordance with the invention (once it has commenced) in the presence of the specified catalyst and activator, is dependent both upon the degree of alkoxylation that is desired (i.e., upon the average adduct number of the product) as well as upon the rate of the alkoxylation reaction. This reaction rate is, in turn, dependent upon such parameters reaction temperature, pressure, and catalyst concentration in the reaction mixture. Under most preferred operating conditions, preparation of an alkoxylate having an average alkylene oxide adduct number of about 3 can typically be accomplished in about ½ to 1 hour, while preparation of a product having an average adduct number of about 12 would require about 4 to 6 hours. These reaction times are merely illustrative and can be substantially reduced by operation at the higher reaction temperatures and/or pressures, although often at the expense of a loss of selectivity in the utilization of the reactants to the desired alkoxylate products. Following the reaction process, the product mixture is usually neutralized by addition of an acid to convert the basic catalyst components to inactive neutral salts. The choice of the acid used is not critical. Examples of suitable acids known to the art for this service include acetic acid, sulfuric acid, phosphoric acid, and hydrochloric acid. Acetic acid is generally preferred.

The invention is further illustrated by the following examples.

EXAMPLE 1

An alkoxylation process in accordance with the invention was conducted in a 300 ml stainless steel autoclave reactor. The alkanol reactant for this process was a NEODOL 23 Alcohol (trademark of and sold by Shell Chemical Company), characterized as a mixture of primary, 80% linear (20% branched) alkanols containing twelve and thirteen carbon atoms (about 40%m $C_{12}$, 60% m $C_{13}$) produced by hydroformylation. Ethylene oxide was employed as the alkylene oxide reactant. The catalyst was magnesium ethoxide.

For use as reaction activator there was prepared from the alkanol reactant an alkoxylate (ethoxylate) of low alkylene (ethylene) oxide adduct number by the following procedure. First, 0.1 gram of 85 percent purity potassium hydroxide (1.51 millimoles KOH) was added to 60 grams (309 millimoles) of the alkanol reactant in a multineck round bottom flask. The resulting liquid solution was dried to a water content of about 18 ppm by sparging with nitrogen at 130° C. for 30 minutes, and then transferred to the autoclave reactor maintained under a nitrogen atmosphere. The reactor was heated to about 170° C. and pressurized by addition of nitrogen and the gaseous ethylene oxide to a total pressure of about 70 psig (55 psia nitrogen and 30 psia ethylene oxide). As the ethoxylation reaction commenced, ethylene oxide was added at a rate sufficient to maintain constant total pressure in the system. Over a 15 minute period, 13.6 grams (309 millimoles) of ethylene oxide were added. Ethylene oxide addition was then discontinued and the reaction mixture maintained at 170° C. for an additional 30 minutes to consume unreacted ethylene oxide. The mixture was cooled to 50° C., transferred under nitrogen to a sample bottle and neutralized with acetic acid to a pH of 6.0. Chromatographic analysis indicated a mixture containing about 46%w of residual alkanol reactant and 54%w of alkoxylate (ethoxylate) molecules having an average adduct number of about 1.85.

For alkoxylation in accordance with the invention, 60 grams of alkanol reactant were blended with 10 grams of the alkoxylate/alkanol mixture prepared as described above. The resulting blend thus contained 64.6 grams of alkanol reactant and, as reaction activator, 5.4 grams of an alkoxylate having an average adduct number of about 1.85. On a molar basis, the blend contained about 6%m activator, calculated on alkanol reactant. This alkanol and activator solution was dried to about 30 ppm water. At 130° C., 2.0 grams of magnesium ethoxide (17.5 millimoles) were dissolved in this solution producing a clear, colorless, nonviscous liquid. The catalyst concentration was about 5.2%m, calculated on the 64.6 grams of alkanol reactant. Ethanol resulting from a transalcoholysis reaction of the catalyst was removed from the solution by sparging with nitrogen for 30 minutes at 130° C. After transfer of the solution to the autoclave reactor the system was sealed, heated to 170° C. and pressurized to a total pressure of about 70 psig (55 psia $N_2$, 30 psia ethylene oxide reactant). Ethoxylation proceeded without an induction period. A total of 103 grams (2.35 moles) of ethylene oxide was added over three hours, at a rate which maintained the 70 psig total pressure in the reactor. The reaction was continued at 130° C. for a further 30 minutes, without ethylene oxide addition, to consume unreacted reactant remaining in the system. The product mixture was then cooled, removed from the autoclave and neutralized with acetic acid. Analysis showed that alkoxylation was essentially complete—only 2.5%w residual alkanol remained in the product mixture. The product has an average adduct number of about 6.4 and contained, as the only observed by-product, about 0.2%w of polyethylene glycols.

Comparative Example A

An alkoxylation process was attempted under the general procedures of Example 1. In this case, however, the process was carried out in the absence of any alkoxylate activator and thus not in accordance with the invention. A mixture of 65 grams of the dried alkanol reactant and 2.0 grams magnesium ethoxide was prepared and sparged with nitrogen for one hour at 130° C. The mixture was then contacted with ethylene oxide in the autoclave reactor maintained under a temperature of 170° C. and a total pressure of about 70 psig (55 psia nitrogen and 30 psia ethylene oxide). No alkoxylation was observed to take place over a period of five hours.

EXAMPLE 2

In another example of the invention, the mixture containing 46%w of alkanol reactant and 54%w of an ethoxylate of 1.85 average adduct number, prepared in the course of activator preparation for Example 1 was subjected to further ethoxylation. This alkanol/ethoxylate mixture was first dried to 30 ppm water by sparging with nitrogen. Then, at a temperature of 130° C., 2.0 grams (17.5 millimoles) of magnesium ethoxide, as catalyst, was dissolved in about 68.7 grams of the dried mixture to give a solution containing 31.6 grams of alkanol reactant, 37.1 grams of ethoxylate activator having an average adduct number of 1.85 (an activator concentration of about 84%m, calculated on alkanol), and 2.0 grams catalyst (10.8%m calculated on alkanol reactant).

This alkanol reactant, activator and catalyst mixture was reacted with an ethylene oxide reactant according to the invention, and under the same general procedures as applied in Example 1. The reaction commenced without an induction period. Over a 2.0 hour period, 70 grams of ethylene oxide were introduced into the reactor. The final product mixture had an adduct number of 6.7 and contained only 2.1%w residual alkanol reactant and 0.4%w polyethylene glycols.

EXAMPLE 3

Another example of the process of the invention was carried out essentially as described in Example 2. In this case, however, magnesium methoxide, instead of magnesium ethoxide, was utilized as catalyst in a quantity of 1.77 grams and about a 5.2%m concentration, calculated on alkanol. The product was found to have an average adduct number of 6.5 and to contain only about 2.1%w of residual alkanol and 0.4%w of polyethylene glycols.

EXAMPLE 4

To a dried (by sparging) mixture containing 24.9 grams of NEODOL 23 alkanol reactant and 70.8 grams (175%m on alkanol reactant) of an ethoxylate activator having an average adduct number of about 2.75, was added 2.0 grams (13.6%m on alkanol) of magnesium ethoxide catalyst. After nitrogen sparging to remove ethanol, the mixture was reacted with ethylene oxide in accordance with the invention and under the general procedures of Example 1. After the alkoxylation reaction commenced (without an induction period), 67 grams of ethylene oxide were added to the reactor over a period of 2.5 hours. Analysis of the alkoxylate product indicated an average alkylene oxide adduct number of 6.0, a residual alkanol content of 2.2%w, and a polyethylene glycol content of 0.8%w.

EXAMPLE 5

To a dried mixture containing 44.2 grams of the NEODOL 23 alkanol reactant and 27.2 grams (43.5%m on alkanol reactant) of an ethoxylate activator having an average adduct number of about 1.84, was added 2.0 grams (7.7%m on alkanol) of the magnesium ethoxide catalyst. The mixture was sparged and then reacted with ethylene oxide in accordance with the invention and under the general procedures of Example 1. A total of 87 grams of ethylene oxide reactant were added to the reactor over a three hour period. The product mixture had an average ethylene oxide adduct number of about 6.8 and contained only 1.5%w of residual alkanol and 0.05%w of polyethylene glycols.

EXAMPLE 6

Another example of a process conducted in accordance with the invention is described to illustrate other aspects of the practice of the invention.

For this example, dibutyl magnesium was employed as catalyst (or catalyst precursor) and diethylene glycol, monomethyl ether (an ethoxylate of methanol having an ethylene oxide adduct number of 2) as reaction activator. The catalyst and the activator were premixed—24 milliliters of a 0.5 molar solution of dibutyl magnesium in heptane (containing a total of 12 millimoles of dibutyl magnesium) was added dropwise to a solution of 2.88 grams (24 millimoles) of the activator in 20 milliliters of tetrahydrofuran. The mixture was refluxed for one hour. Solvent was then evaporated from the mixture and the remainder, a clear, colorless, non-viscous solution, was added to 65 grams (335 millimoles) of the NEODOL 23 alkanol reactant described in Example 1. The catalyst and activator solution in the alkanol was transferred to the autoclave for reaction with ethylene oxide at 170° C., and 70 psig total pressure (55 psia $N_2$, 30 psia ethylene oxide). The reaction mixture contained about 3.6%m of the catalyst and about 7.2%m of the activator, both calculated on alkanol reactant. After addition of ethylene oxide to the reactor, no reaction was observed for 1.5 hours. An alkoxylation reaction then proceeded slowly over the next 30 minutes until, after two hours, a good rate of reaction was observed. Two additional hours of reaction converted 88.5% of the alkanol reactant to yield an ethoxylate product having an average adduct number of about 2.7. The product mixture also contained about 8%m, calculated on ethoxylate of $C_{12}$ and $C_{13}$ alkanol, of a roughly 5 mole ethylene oxide adduct of methanol which was produced by ethoxylation of the activator.

I claim as my invention:

1. A process for the preparation of alkanol alkoxylates which comprises reacting, in a reaction mixture of basic pH, an alkanol reactant comprising one or more alkanols having carbon numbers in the range from about 8 to 18, inclusive, with an alkylene oxide reactant comprising one or more alkylene oxides having carbon numbers in the range from 2 to 4, inclusive, in the presence of a catalytically-effective amount of one or more soluble basic compounds of magnesium, and additionally in the presence of as reaction activator at least about 2.0 percent by mole, calculated on alkanol reactant, of one or more alkoxylates as are produced by the alkoxylation reaction of $C_8$ to $C_{18}$ alkanols and $C_2$ to $C_4$ alkylene oxides.

2. The process of claim 1, wherein the basic soluble compound of magnesium is selected from the group consisting of alcoholate, ammoniate, amide, thiolate, thiophenoxide, nitride, thiocyanate and carboxylate compounds and the substances to which such compounds are converted in situ in the reaction mixture.

3. The process of claim 2, wherein the basic soluble compound of magnesium is selected from the group consisting of alcoholates and substances to which the alcoholates are converted in situ in the reaction mixture.

4. The process of claim 3, wherein the basic soluble compound of magnesium is selected from the group consisting of alkoxides having a carbon number in the range from 1 to about 30 and the substances to which the alkoxides are converted in situ in the reaction mixture.

5. The process of claim 1, wherein the reaction activator is an alkoxylate of one or more $C_8$ to $C_{18}$ alkanols having in the alkoxylate molecules from 1 to about 30 adducts of one or more alkylene oxides selected from the class consisting of ethylene oxide and propylene oxide.

6. The process of claim 2, wherein the reaction activator is an alkoxylate of one or more $C_8$ to $C_{18}$ alkanols having in the alkoxylate molecules from 1 to about 5 adducts of one or more alkylene oxides selected from the class consisting of ethylene oxide and propylene oxide.

7. The process of claim 3, wherein the reaction activator is an alkoxylate of one or more $C_8$ to $C_{18}$ alkanols having in the alkoxylate molecules from 1 to about 3 adducts of ethylene oxide.

8. The process of claim 1, claim 2, claim 5, or claim 7, wherein the amount of the soluble basic magnesium compound present in the reaction mixture is between about 0.2 and 20 percent by mole, calculated on moles of alkanol reactant, and the amount of activator present in the reaction mixture is at least about 3 percent by mole, calculated on moles of alkanol reactant.

9. The process of claim 8, wherein the amount of the activator present in the reaction mixture is at least about 5 percent by mole.

10. The process of claim 9, wherein the amount of the activator present in the reaction mixture is at least about 7 percent by mole.

11. The process of claim 10, wherein the amount of the soluble basic magnesium compound present in the reaction mixture is between about 0.5 and 15 percent by mole, calculated on moles of alkanol reactant.

12. A process for the preparation of alkanol alkoxylates which comprises reacting, in a reaction mixture of basic pH, at a temperature between about 150° and 190° C. an alkanol reactant comprising one or more alkanols having carbon numbers in the range from about 10 to 16, inclusive, with ethylene oxide in the presence of between about 0.2 and 20 percent by mole, calculated on alkanol reactant, of one or more soluble basic compounds of magnesium, and additionally in the presence of at least about 6 percent by mole, calculated on alkanol reactant, of an ethoxylate of one or more $C_{10}$ to $C_{16}$ alkanols having an average ethylene oxide adduct number less than 5.

13. A process for the preparation of alkanol alkoxylates which comprises steps for
(a) reacting, in a reaction mixture of basic pH, an alkanol reactant comprising one or more alkanols having carbon numbers in the range from about 6 to 30, inclusive, with an alkylene oxide reactant comprising one or more alkylene oxides having carbon numbers in the range from 2 to 4, inclusive, in the presence of a catalytically-effective amount of one or more soluble basic compounds of magnesium, and additionally in the presence of as reaction activator at least about 2.0 percent by mole, calculated on alkanol reactant, of one or more alkoxylates as are produced by the alkoxylation reaction of $C_6$ to $C_{30}$ alkanols and $C_2$ to $C_4$ alkylene oxides, and
(b) neutralizing the resulting reaction mixture.

14. The process of claim 13, wherein the basic soluble compound of magnesium is selected from the group consisting of alcoholate, ammoniate, amide, thiolate, thiophenoxide, nitride, thiocyanate and carboxylate compounds and the substances to which such compounds are converted in situ in the reaction mixture.

15. The process of claim 14, wherein the basic soluble compound of magnesium is selected from the group of consisting of alcoholates and substances to which the alcoholates are converted in situ in the reaction mixture.

16. The process of claim 15, wherein the basic soluble compound of magnesium is selected from the group consisting of alkoxides having a carbon number in the range from 1 to about 30 and the substances to which the alkoxides are converted in situ in the reaction mixture.

17. The process of claim 13, wherein the reaction activator is an alkoxylate of one or more $C_8$ to $C_{18}$ alkanols having an the alkoxylate molecules from 1 to about 5 adducts of one or more alkylene oxides selected from the class consisting of ethylene oxide and propylene oxide.

18. The process of claim 1, wherein the amount of the soluble basic magnesium compound present in the reaction mixture is between about 0.2 and 20 percent by mole, calculated on moles of alkanol reactant, and the amount of activator present in the reaction mixture is at least about 3 percent by mole, calculated on moles of alkanol reactant.

19. The process of claim 18, wherein the amount of the activator present in the reaction mixture is at least about 5 percent by mole.

20. The process of claim 19, wherein the amount of the soluble basic magnesium compound present in the reaction mixture is between about 0.5 and 15 percent by mole, calculated on moles of alkanol reactant.

* * * * *